Nov. 5, 1957 L. E. GAVELLO Plant Pat. 1,658

ESCALLONIA PLANT

Filed Feb. 25, 1957

INVENTOR.
LOUIS E. GAVELLO
BY
Bruce & Brooler
HIS ATTORNEYS

United States Patent Office

Plant Pat. 1,658
Patented Nov. 5, 1957

1,658

ESCALLONIA PLANT

Louis E. Gavello, Richmond, Calif.

Application February 25, 1957, Serial No. 642,324

1 Claim. (Cl. 47—60)

My invention relates to a new and distinct variety of evergreen Escallonia plant of shrub type which was initially originated by me as a selective seedling and thereafter effectively reproduced by me from cuttings at Richmond, California.

My new shrub is a cross between Escallonia Donard's seedling and *Escallonia organensis,* both unpatented. The parent Escallonia Donard's seedling is a medium fast grower of loose form and small leaf, while the parent *Escallonia organensis* is a fast grower, also of loose form, and producing large leaves.

The primary distinctions of my new variety over the parent plants are that it is very compact from the base up, very heavily foliated, and is further characterized by its slower growth, thus making it a very important shrub for foundation plantings, group plantings, and informal hedges.

It grows well in windy areas; also does well in very moist soil, and can withstand wide changes in temperature.

While the parent plants have regular flowering periods, my new variety in the bay area around San Francisco, bears blooms throughout the year.

Figure 1:
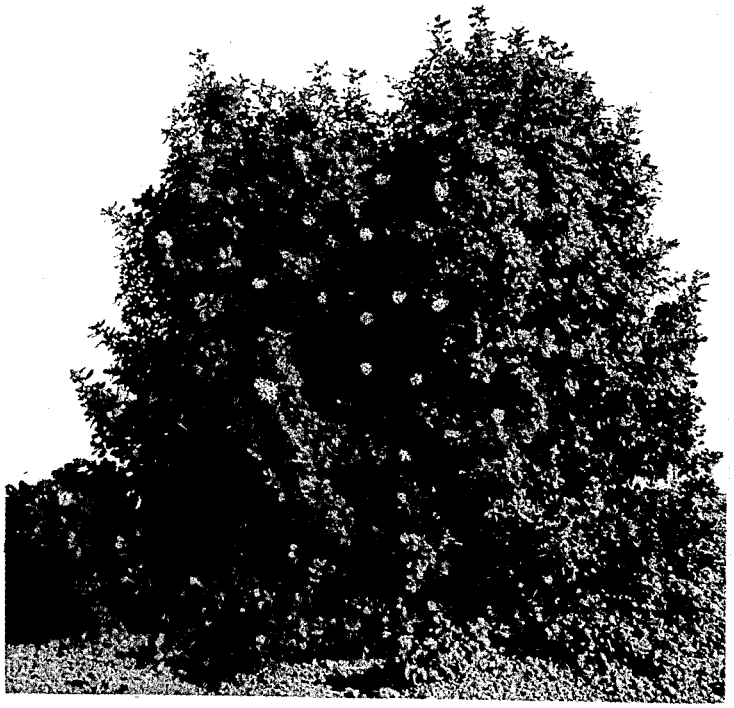
Figure 2:
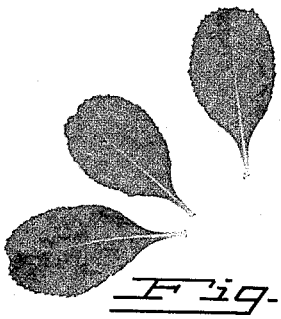
Figure 3:
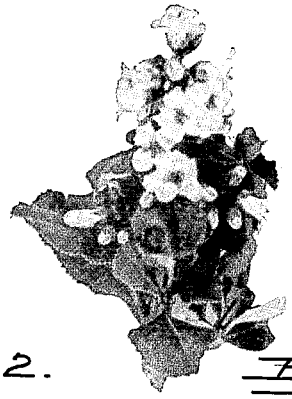

The accompanying illustrations show in Figure 1 a typical plant of the new variety in color, though the color reproduction in spots shows a little too much blue. In Figure 2, is illustrated in color, representative leaves of the new variety, while in Figure 3 is shown in color, a portion of a branch bearing flowers both in bud and in full bloom.

In the following specific description of my new variety, color definitions are more precisely identified by plate numbers to be found in Dictionary of Color, 1950, by Maerz and Paul.

*Escallonia hybrid*

Growth habit:

1. Height and spread about 4½ feet.
2. Compact habit but spreading from base with present year shoots, more or less horizontally at the basal portion and vertically at apex of shoot.
3. Young shoots angular and with coarse glandular punctate hairs.

Leaves:

1. Evergreen, oval, scarcely narrowed toward petiole.
2. Color—Chrome Green (Plate 24–12–H).
3. Length—1 to 1¾ inches long.
4. Width—¾ to 1⅛ inches wide.
5. Petiole—¼ to ⅜ inch long.
6. Margins of leaves sharply serrate, pinnately veined with about seven pairs of secondary veins, conspicuously punctate on lower leaf surface.

Inflorescence paniculate, about 2 inches tall.

Flowers:

1. Pinkish or Rose (Plate 1–5A), buds deeply pink tinted at their apices and as flowers open, petals are very light pink at their bases and pink along their apical margins.
2. Petals about 7/16 inch long.
3. Claw of petal about ¼ inch long, spreading.
4. Broadened part of petal about 3/16 inch long.
5. Spread of petals about ½ inch.
6. Hypanthium about ⅛ inch long.
7. Sepals about ⅛ inch long, deltoid.
8. Stamens and styles about the same length as the claw of the petal and just protruding from the connate claws of the petals.

Having thus described my invention and discovery, I claim:

A new and distinct variety of Escallonia plant substantially as herein described and characterized particularly by its compact habit of growth and slower rate of development as compared with the parent plants.

No references cited.